March 18, 1975 B. J. MACHIN Plant Pat. 3,692
CHRYSANTHEMUM PLANT
Filed July 23, 1973
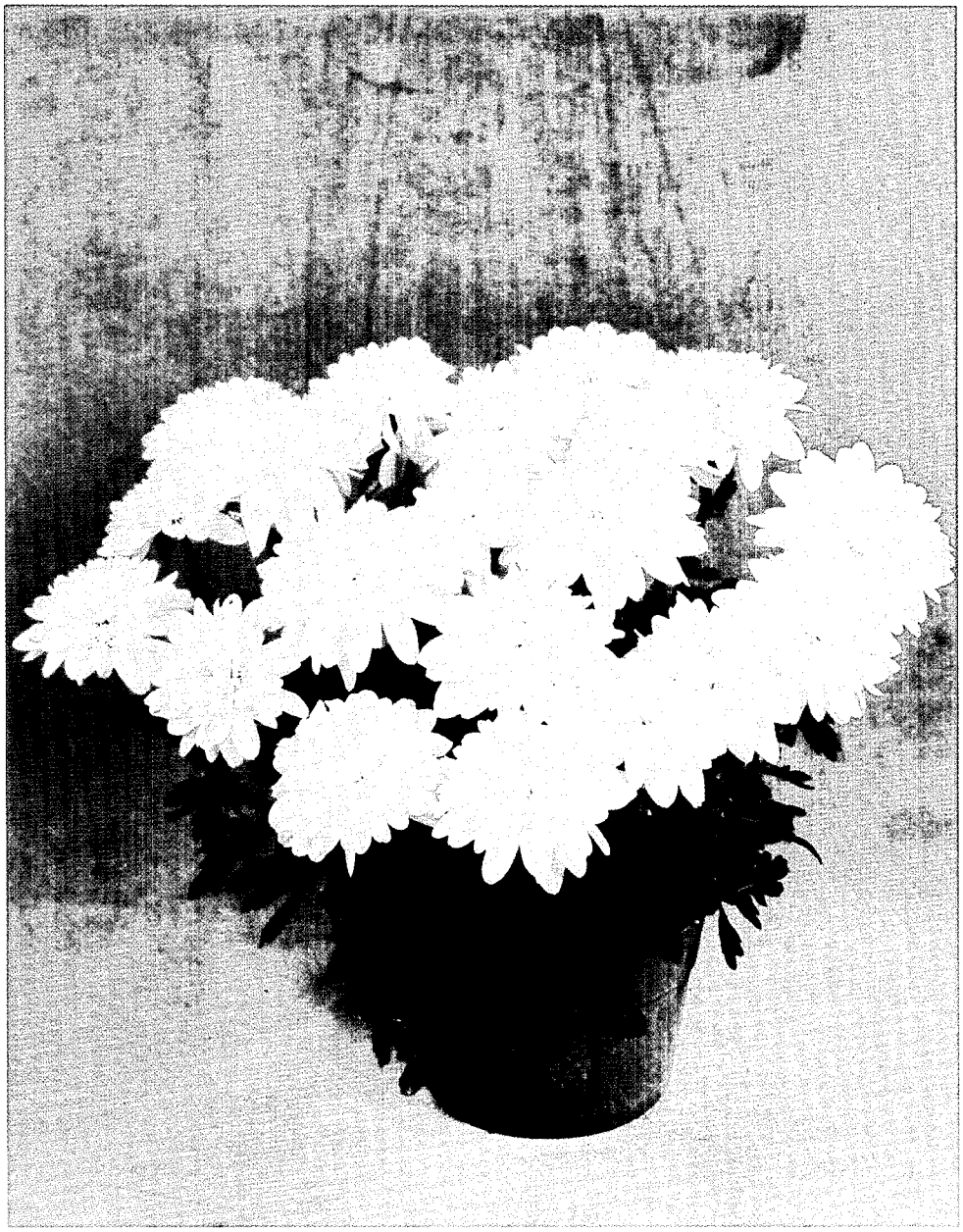

United States Patent

Plant Pat. 3,692
Patented Mar. 18, 1975

3,692

CHRYSANTHEMUM PLANT

Barrie John Machin, East Broyle Estate, Chichester, England, assignor to Framptons Nurseries Limited, Worthing, England

Filed July 23, 1973, Ser. No. 381,666
Int. Cl. A01h *5/00*
U.S. Cl. Plt.—78 1 Claim

ABSTRACT OF THE DISCLOSURE

This invention relates to a new and distinctive variety of *Chrysanthemum morifolium* Bailey, pot type, known as Yellow Aramis.

The new variety is a sport from the variety Aramis which was originated by me from a cross made in 1966 between the unpatented variety Redcap and the unpatented variety Frolic, the former being the seed parent the latter being the pollen parent. The new variety Yellow Aramis was a sport induced by irradiation from Aramis in July 1971.

The variety Aramis resulted from an extensive breeding program with the object of producing improved varieties for year-round pot chrysanthemum production with more uniformity and improved response compared with the existing varieties.

Yellow Aramis is distinguished from Aramis by its distinctly yellow color.

Yellow Aramis has the following improved characteristics over Bright Golden Anne, the most similar existing variety with which I am familiar:

1. It has a shorter internode length and it is thus easier to control the height of the plant by day length or chemical control measures.

2. Although the flowers are smaller, form is improved and there are more petals in each flower. On average, more flowers per plant are obtained following removal of the growing tip.

3. Response is more uniform in poor winter light conditions, i.e., when five cuttings are planted in each pot there is less difference between the individual flower dates of each individual plant in Yellow Aramis than in Bright Golden Anne.

4. Since the petals are shorter and thicker in Yellow Aramis than in Bright Golden Anne, the lasting quality of the pot, i.e. the shelf life, tends to be better in the former variety.

Asexual reproduction of this new variety Yellow Aramis, as performed in Sussex, England, by rooting vegetative shoots, shows that the above characteristics are fixed and come true to type through succeeding generations.

The accompanying drawing shows a typical flower of my new variety depicted in color as nearly true as it is reasonably possible to make the same in a color illustration of this character.

The following is a detailed description of the new variety Yellow Aramis with color terminology in accordance with the Royal Horticultural Society color chart, hereinafter referred to as RHS.

Genus: Chrysanthemum.
Species: *Morifolium* Bailey.
Type: Pot.
Class: Decorative.
Breeding: The original seedling Aramis resulted from a cross between the variety BGA Redcap and the variety BGA Frolic, the former being the seed parent the latter being the pollen parent. The cross was made in 1966 at Framptons Nurseries Ltd., Forbridge Nursery, Chichester, Sussex, England. The variety Yellow Aramis was induced by irradiation from Aramis in July, 1971.
Propagation: Holds its distinguishing characteristics through succeeding generations by rooting vegetative shoots.
Flower: When grown and observed in Sussex, England, in 3½ inch pots and pinched, up to six flowers per plant are formed. When 5 plants are planted per 5 inch pot four to five flowers are borne on each plant.
Bloom:
*Size.*—Average diameter is 8 to 19 cm. when fully open.
*Petallage.*—Decorative with approximately 250 ray petals and five disc petals.
*Form.*—Decorative.
*Petals.*—Medium length, broad, overlapping, blunt, flat, and of medium texture.
Color of open bloom:
*Inner face of fully expanded petal.*—RHS 6B
*Outer face of fully expanded petal.*—RHS 6D.
*Inner face of young petal.*—RHS 7A.
*Outer face of young petal.*—RHS 6B.
Response group: 10 weeks.
Temperature tolerance: 55 to 60° F. at night.
Plant: Stocky, well branched habit of growth.
Foliage: Medium quality, average internode length 1½ to 2 cm. Medium size. Color RHS 137C. Medium texture.
Stem: Thick and strong. Color 145C at flowering.

I claim:

1. A new and distinct variety of *Chrysanthemum morifolium* Bailey, substantially as shown and described, characterized particularly as to novelty by the unique combination of a yellow color, short internode length, and uniform response in poor winter light conditions.

No references cited.

ROBERT E. BAGWILL, Primary Examiner